United States Patent [19]
Klaue et al.

[11] Patent Number: 5,810,823
[45] Date of Patent: Sep. 22, 1998

[54] OSTEOSYNTHETIC BONE PLATE AND LOCK WASHER

[75] Inventors: Kaj Klaue, Heidelberg, Germany; Jeffrey W. Mast, Grosse Point Park, Mich.

[73] Assignee: Synthes (U.S.A.), Paoli, Pa.

[21] Appl. No.: 800,080

[22] Filed: Feb. 12, 1997

Related U.S. Application Data

[63] Continuation-in-part of Ser. No. 302,968, Sep. 12, 1994, abandoned.

[51] Int. Cl.⁶ .................................................. A61B 17/00
[52] U.S. Cl. ............................................................ 606/69
[58] Field of Search ................... 606/69, 70, 71, 606/72, 73, 65, 66, 67, 68

[56] References Cited

U.S. PATENT DOCUMENTS

| | | |
|---|---|---|
| 3,489,143 | 1/1970 | Halloran ...................... 606/67 |
| 4,373,309 | 2/1983 | Lutz . |
| 4,484,570 | 11/1984 | Sutter et al. ................. 606/71 |
| 4,513,744 | 4/1985 | Klaue . |
| 5,057,111 | 10/1991 | Park . |
| 5,129,899 | 7/1992 | Small et al. . |
| 5,167,532 | 12/1992 | Bruno et al. . |
| 5,234,431 | 8/1993 | Keller ........................ 606/70 |
| 5,269,784 | 12/1993 | Mast . |
| 5,591,168 | 1/1997 | Judet et al. .................. 606/65 |

FOREIGN PATENT DOCUMENTS

| | | |
|---|---|---|
| 0 301 489 A1 | 2/1989 | European Pat. Off. . |
| 0 360 139 A2 | 3/1990 | European Pat. Off. . |
| 0 410 309 A1 | 1/1991 | European Pat. Off. . |
| 0 507 162 A1 | 10/1992 | European Pat. Off. . |
| 30 27 148 A1 | 12/1981 | Germany . |
| 35 09 417 A1 | 9/1986 | Germany . |
| WO 89/04150 | 5/1989 | WIPO . |
| WO 90/12547 | 11/1990 | WIPO . |
| WO 94/16634 | 8/1994 | WIPO . |

*Primary Examiner*—Guy V. Tucker
*Attorney, Agent, or Firm*—Fish & Richardson P.C.

[57] ABSTRACT

A lock washer for attaching a bone screw to a bone plate. The lock washer includes a body having a central axis and a borehole having internal threading for receiving the bone screw. The lock washer includes a lower section adapted to abut the surface of a bone, and an upper section shaped to be retained in a plate borehole. An osteosynthetic system including a bone plate having an upper surface, a lower surface to be positioned facing the bone, and a lock washer is also disclosed. In addition, an osteosynthetic bone plate having an upper surface, a lower surface, and boreholes extending through the bone plate from the upper surface to the lower surface is disclosed. Boreholes are provided with hollow protrusions extending beyond the lower surface of the bone plate and having an internal threading for receiving a bone screw.

19 Claims, 6 Drawing Sheets

OSTEOSYNTHETIC BONE PLATE AND LOCK WASHER

CROSS REFERENCE TO RELATED APPLICATIONS

This application is a continuation-in-part of U.S. Ser. No. 08/302,968, filed Sep. 12, 1994 now abandoned, the contents of which are incorporated by reference in their entirety.

BACKGROUND OF THE INVENTION

The invention relates generally to an osteosynthetic bone plate and a lock washer for use with an osteosynthetic bone plate.

Many bone plates employed in osteosynthesis are attached directly to the bone only by bone screws, and are held to the bone solely by the bone screw and the resulting friction between the bone plate and the bone. In such situations, the bone screws are not fixed rigidly to the bone plate because the bone screws are simply anchored in the bone. Loosening of the screws in the bone or a resorption of the bone can, therefore, easily lead to a loosening of the bone plate itself.

For example, certain known bone plate screws pass completely through the bone to be secured by a nut attached to the end of the screw that is remote from the screw head. This method, however, does not provide any direct fixation between the screw and plate. Rather, it causes a compression of the bone lying between the nut and the plate and penetrated by the screw.

Nevertheless, in some situations, it is desirable to fix the bone screw rigidly to the bone plate to avoid any subsequent loosening. It is also desirable to reduce the contact surface adjoining the bone for the purpose of improving vascularity in a manner that minimizes damage to the bone surface.

SUMMARY OF THE INVENTION

In general, in one aspect, the invention features a lock washer for attaching a bone screw to a bone plate. The lock washer includes a body having a central axis and a borehole having internal threading for receiving the bone screw. The lock washer includes a lower section adapted to abut the surface of a bone, and an upper section shaped to be retained in a plate borehole. The average width or diameter of the lower section of the lock washer is preferably less than the average width or diameter of the upper section. Various implementations and features of the lock washer are described in detail below.

In another aspect, the invention features an osteosynthetic system including a bone plate having an upper surface and a lower surface to be positioned facing the bone, and a lock washer.

In yet a further aspect, the invention features an osteosynthetic bone plate having an upper surface, a lower surface, and boreholes extending through the bone plate from the upper surface to the lower surface. Each of at least two boreholes is provided with a hollow protrusion extending beyond the lower surface of the bone plate. In addition, each protrusion has an internal threading for receiving a bone screw inserted through the upper surface and borehole of the bone plate. Additional features are described below.

In various implementations, the invention provides one or more of the following advantages. The lock washer can be used with multiple types of bone plates and bone screws. Additionally, use of the lock washer can be limited to specific boreholes in the bone plate depending upon the particular application. The lock washer can, therefore, be used intraoperatively as well.

The lock washer can also serve as a spacer between the bone plate and the bone. The reduced contact surface permits improved blood flow and thus, quicker healing. Mechanical stability of the lock washer in the contact area near the bone can be increased because the surface of the lock washer which is adjacent the bone is also adjacent the surface of the bone through which the bone screw passes.

In addition, by using the lock washer, it is possible to place the bone plate at a specified distance from the bone, resulting in a so-called ultra-low profile external fixator. Furthermore, the rigid fixation prevents undesired deformities, which can occur with axial compression upon rotation of the screw. The lock washer also permits a certain degree of energy storage when pressure is exerted on the fracture. Thus, it is possible to exert a compression effect which lasts longer. Such energy storage can also remove the load on screws, such as tension bolts, that are positioned in the conventional way through a plate hole. In addition, the lock washer allows the bone screw to tilt laterally relative to the central axis of the plate hole without providing additional accessories.

Various implementations of the osteosynthetic bone plate with the hollow protrusions can also provide many of the advantages discussed above. In addition, the bone plate with the hollow protrusions provides a single unitary piece which can be simpler and more convenient to use in some applications. The lock washer and/or the bone plate can be employed in the following exemplary ways:

(a) With osteoporotic bones or bones with a thin corticalis. A premature loosening, which occasionally takes place through cyclic loading, can be avoided because a rigid fixation is present between the plate and screw.

(b) With a bone defect in the superficial corticalis, which can appear, for example, with a comminuted fracture in the bone.

(c) With an indication of former "blade plates."

Additional features and advantages of the invention will be evident from the detailed description and accompanying drawings.

DESCRIPTION OF THE PREFERRED EMBODIMENTS

Figure 1:
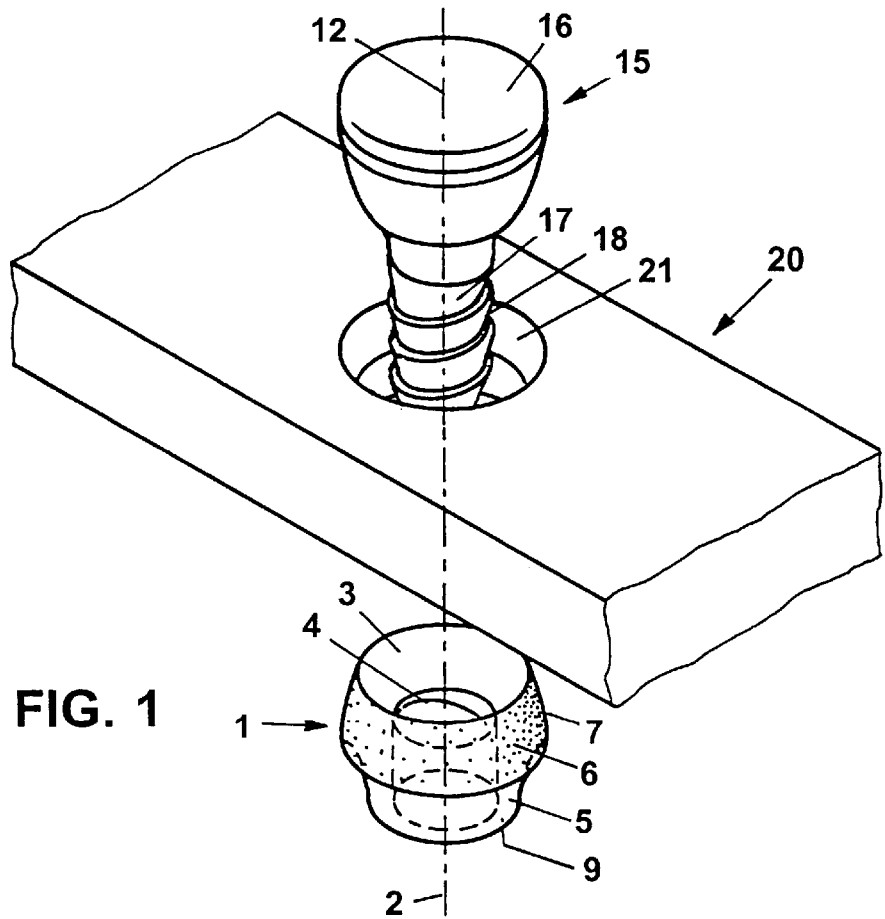
FIG. 1 shows an exploded perspective of an osteosynthetic system according to the invention.
Figure 2:
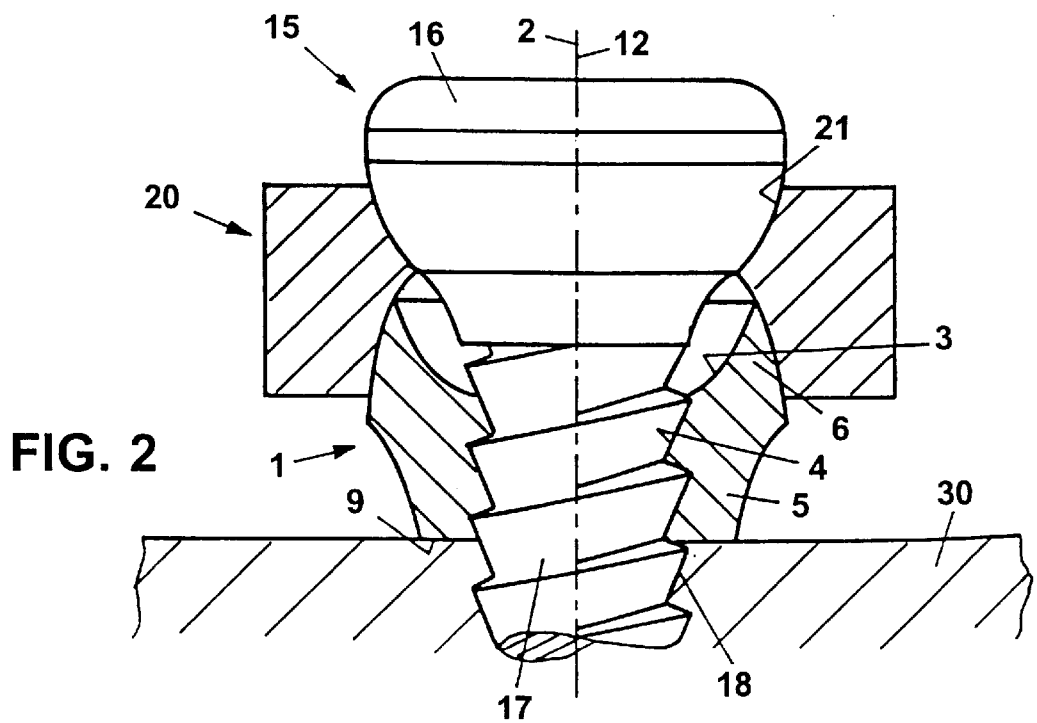
FIG. 2 shows a cross-section of FIG. 1.

FIGS. 1 and 2 illustrate a bone plate 20, a bone screw 15 for insertion into a bone 30, and a lock washer 1. The lock washer 1 is a unitary piece having a central axis 2, a central borehole 3 with an interior threading 4 which matches an external threading 18 on the shaft 17 of the bone screw 15, a lower section 5 and an upper section 6. The lock washer 1 has a surface 9 which is adjacent the bone 30 when the bone screw 15 is fully inserted, through the plate 20 and the lock washer 1, into the bone 30. An outer surface 7 of the upper section 6 is tapered conically such that the outer diameter of the upper section 6 decreases with increasing distance from the surface 9.

The bone plate 20 has at least one borehole, such as the borehole 21, which extends through the plate 20 in a direction substantially perpendicular to the plane of the plate 20. The lower portion of the borehole 21 is also tapered conically such that the upper section 6 of the lock washer 1 can be inserted into the borehole 21 in an essentially tight or lock-forming manner. The interior threading is essentially fully accommodated in the lower section 5. Furthermore, the surface 7 of the upper section 6 can be roughened to achieve firm rotational stability within the borehole 21.

The average outer diameter of the lower section 5 of the lock washer 1 is smaller than the average outer diameter of the upper section 6, thereby providing a relatively small surface 9 for contact with the bone 30.

When the shaft 17 of the bone screw 15 is inserted, through the bone plate 20 and the lock washer 1, into the bone 30 as illustrated in FIG. 2, the central axis 2 of the lock washer 1 is substantially aligned with the central axis 12 of the borehole 21. As the bone screw 15 is inserted into the bone 30, the head 16 of the bone screw 15 advances toward, but not does not contact, the lock washer 1.

Figure 3:
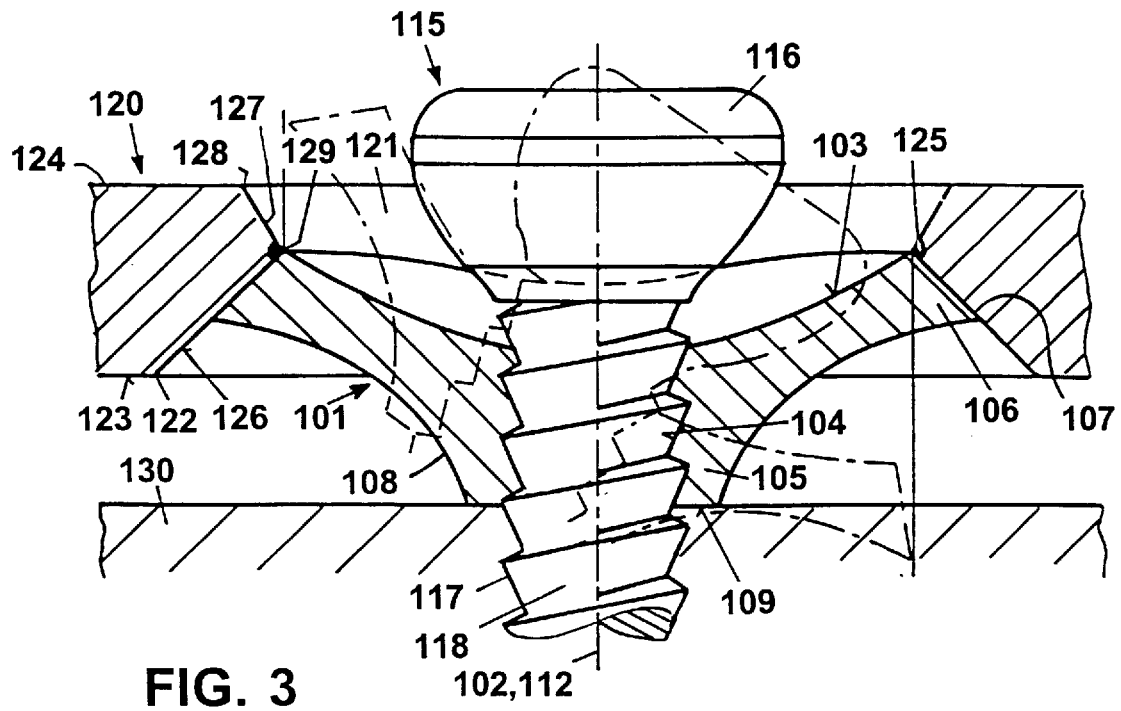
FIG. 3 shows a cross-section of another osteosynthetic system according to the invention.
Figure 4:
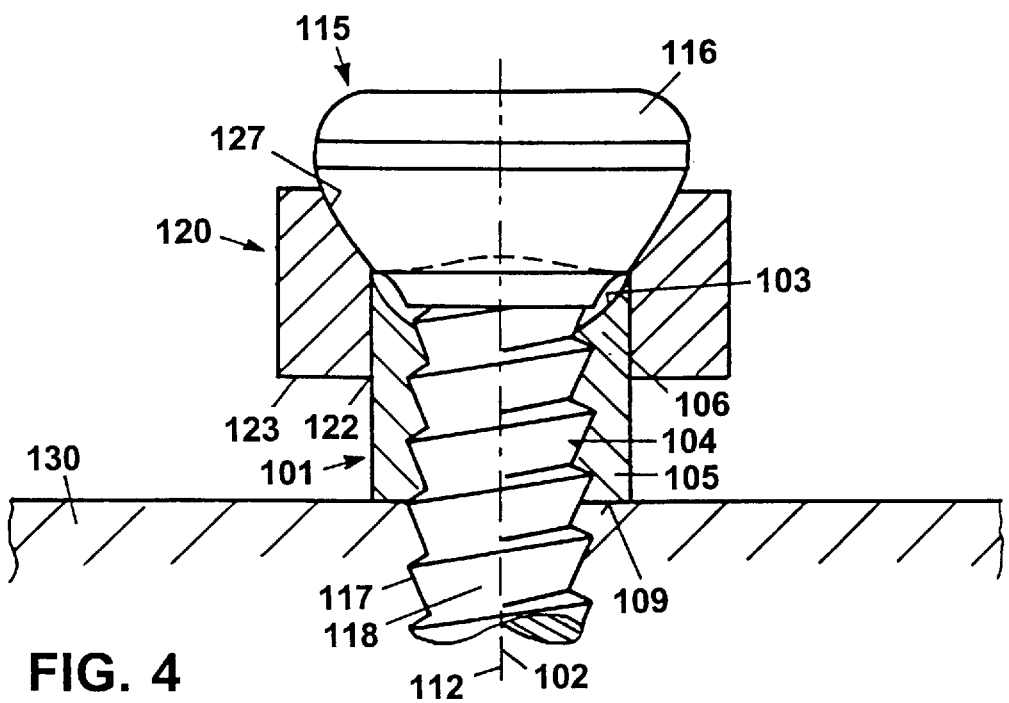
FIG. 4 shows another cross-section of the osteosynthetic system of FIG. 3 taken in a direction perpendicular to the cross-section of FIG. 3.
Figure 5:
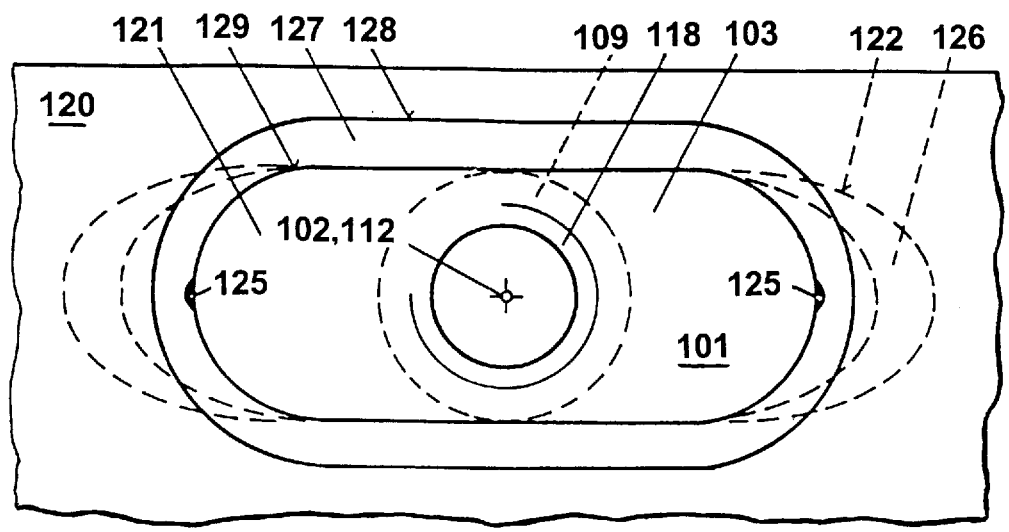
FIG. 5 shows a downward view of the system of FIG. 3.

FIGS. 3–5 illustrate another implementation of a bone plate 120, a bone screw 115 for insertion into a bone 130, and a lock washer 101. The bone plate 120 has a lower surface 123 and an upper surface 124. The bone plate 120 also has at least one borehole, such as the borehole 121, that is essentially ellipse or oval-shaped. As shown in FIG. 3, the inner diameter of the borehole 121 is lengthened in the longitudinal direction of the bone plate 120. Elastic nipples or beads 125, whose function is described further below, are positioned within the bone plate 120 on opposite sides of the borehole 121 at the narrowest longitudinal width 129 of the borehole 121. As seen from FIG. 3, the inner surface 127 of the borehole 121 above the point of narrowest longitudinal width 129 widens to the edge 128 of the borehole 121 at the upper side 124 of the bone plate 120. Similarly, the inner surface 126 of the borehole 121 below the point of narrowest width 129 widens to the edge 122 of the borehole 120 at the lower side 123 of the bone plate 120.

The lock washer 101 is a unitary piece having a central axis 102, a central borehole 103 with an interior threading 104 which matches an external threading 118 on the shaft 117 of the bone screw 115, a lower section 105 and an upper section 106. The lock washer 101 has a surface 109 which is adjacent the bone 130 when the bone screw 115 is fully inserted through the plate 120 and the lock washer 101 into the bone 130.

The lock washer 101, however, is not rotationally symmetrical. Rather, the lock washer 101 is ellipse or oval-shaped to adapt to the geometry of the borehole 121. In the longitudinal direction, the outer surface 107 of the upper section 106 of the lock washer 101 is tapered to match the corresponding slope of the inner surface 126 of the borehole 121 (FIG. 3). The smallest outer diameter of the upper section 106 in the longitudinal direction is approximately the same as the narrowest width 129 of the borehole 121 in the longitudinal direction (FIG. 3). Thus, the outer surface 107 of the upper section 106 of the lock washer 101 fits tightly against the inner surface 126 of the borehole 121 when the lock washer 101 is properly inserted within the bone plate 120.

The outer surface 108 of the lower section 105 of the lock washer 101 can also be tapered to provide a relatively small surface 109 for contact with the bone 130. The relative longitudinal dimensions of the edges 122, 123 of the borehole 121 and the outer surface 107 of the upper section 106 of the lock washer 101 are designed to allow insertion of the lock washer 101 from the upper side 124 of the bone plate 120 as well as from the lower side 123, as explained further below. In particular, the longitudinal diameter of the borehole 121 at its lower edge 122 can be made somewhat larger than the longitudinal diameter of the borehole 121 at its upper edge 124. Similarly, the maximum longitudinal diameter of the upper section 106 can be made somewhat smaller than the longitudinal diameter of the borehole 121 at its lower edge 123.

When a bone screw 115 is properly inserted, through the bone plate 120 and the lock washer 101 and into the bone 130, the central axis 102 of the lock washer 101 is substantially aligned with the central axis 112 of the borehole 121. In this position, the bone screw 115 rests against the inner surface 127 of the borehole 121 in a direction parallel to the longitudinal axis of the bone plate 120 (FIG. 4). As seen, however, from FIG. 3, the bone screw 115 does not contact the inner surface 127 of the borehole 121 in the longitudinal direction when the bone screw 115 is fully inserted.

Insertion of the lock washer 101 from the upper side 124 of the bone plate 120 using the osteosynthetic system of Figs. 3–5 can be performed as follows. First, the lock washer 101 is screwed onto the bone screw 115. With the aid of the screw 115, the lock washer 101 is inserted through the borehole 121 by inclining the central axis 2 of the lock washer 101 somewhat in the direction of the longitudinal axis of the bone plate 120, as shown by the dashed lines in FIG. 3. In this manner, the entire lock washer 101 can be maneuvered past the narrow width 129 of the borehole 121. The lock washer 101 can then be positioned as shown in FIGS. 3–4. The beads 125 help to tightly jam the lock washer 101 temporarily within the bone plate 120 in the desired position so that the lock washer 101 does not fall out of the borehole 121 if the bone screw 115 is removed intraoperatively.

Figure 6:
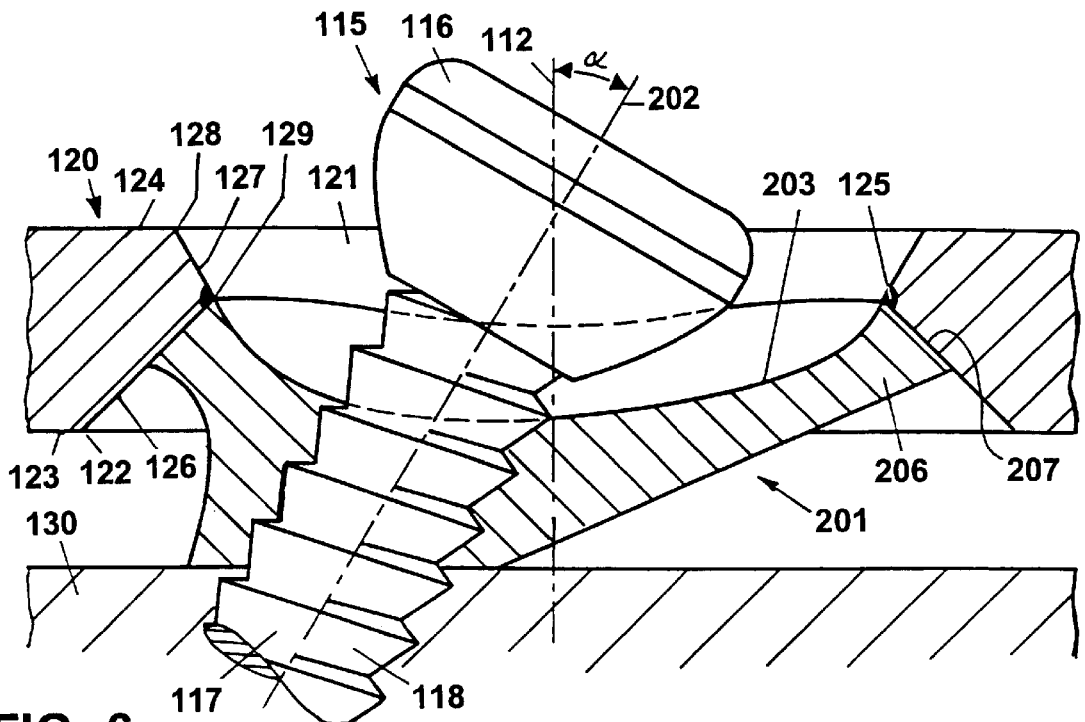
FIG. 6 shows a cross-section of a further implementation of an osteosynthetic system according to the invention.

FIG. 6 shows a further implementation of a lock washer 201 which can be used in combination with the bone plate 120 and the bone screw 115. The lock washer 201 is somewhat similar to the lock washer 101. The lock washer 201, however, is configured to allow the axis of the bone screw 115 to incline relative to the axis 112 of the borehole 121. The lock washer 201 is, therefore, asymmetric, as can be seen from FIG. 6. The lock washer 201 has a central borehole 203 with an axis 202. As shown in FIG. 6, when the tapered outer surface 207 of the upper section 206 of the lock washer 201 is positioned adjacent the inner surface 126 of the borehole 121, the axis 202 of the central borehole 203 is tilted at an angle α relative to the axis 112 of the borehole 121 of the bone plate 120. The angle α conveniently can be 30° C. or less. By using the lock washer 201, the bone screw 115 can be inserted into the bone 130 at an inclined angle.

Figure 7:
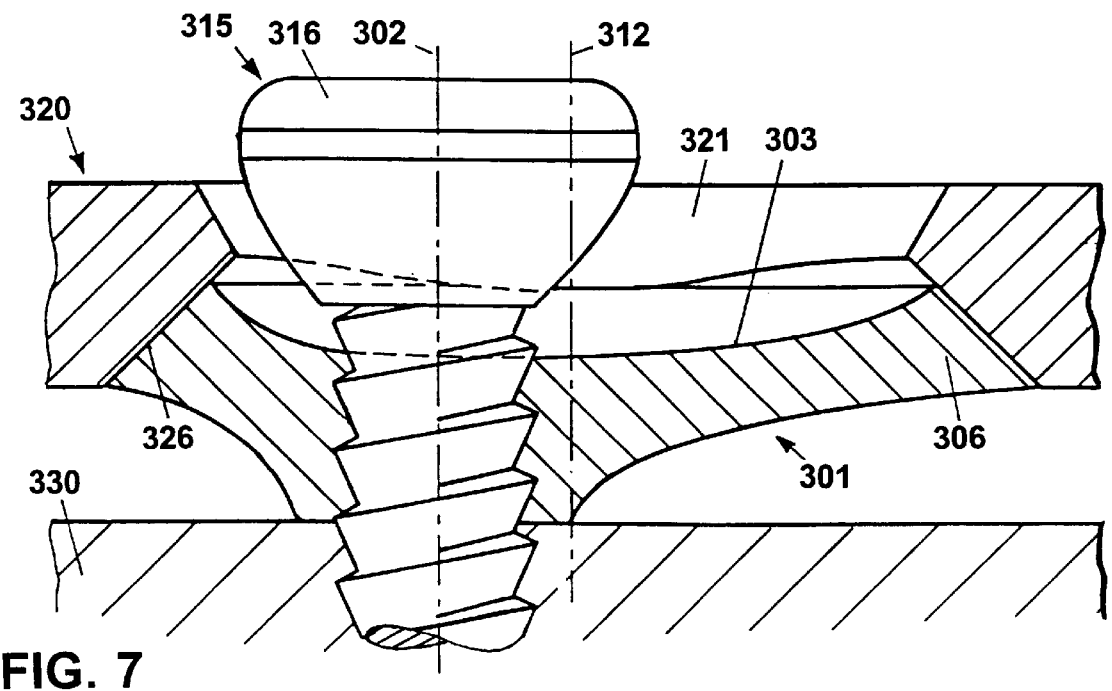
FIG. 7 shows a cross-section of yet another implementation of an osteosynthetic system according to the invention.

FIG. 7 shows yet another design of a lock washer 301 which can be used with a bone plate 320 in which at least one borehole 321 is formed as a camming or glide hole. The principle of such glide holes is described, for example, in Swiss application CH-A5 650 915 and U.S. Pat. No. 4,513,744 to Klaue, which is incorporated herein by reference. The lock washer 301 has an upper section 306 which is asymmetric with respect to the lower section 305 and the central borehole 303. The central axes 302, 312 of the boreholes 303, 321 are both perpendicular to the plane of the bone plate 320. The two axes 302, 312, however, are not coaxial when a screw 315 is properly inserted, through the plate 320 and the lock washer 301, into a bone 330. The camming effect can be used for the screw head 316 as well as the lock washer 301 simultaneously. By tightening the screw 315, the screw head 316 contacts the upper slope of the plate borehole 320, thereby producing a self-correcting effect. The lock washer 301 contacts the oblique undercut surface 326 of the plate borehole 321, thereby producing a camming effect against the bone plate 320 when it is tightened against the screw head.

Figure 8A:
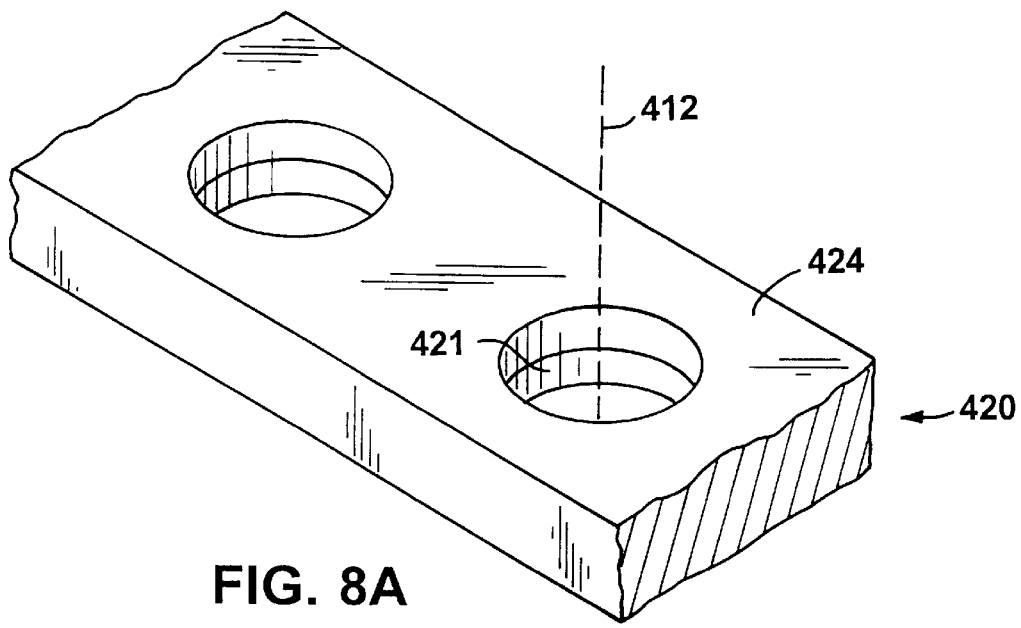
FIGS. 8A and 8B show, respectively, a top view and a bottom view of a bone plate according to the invention.
Figure 8B:
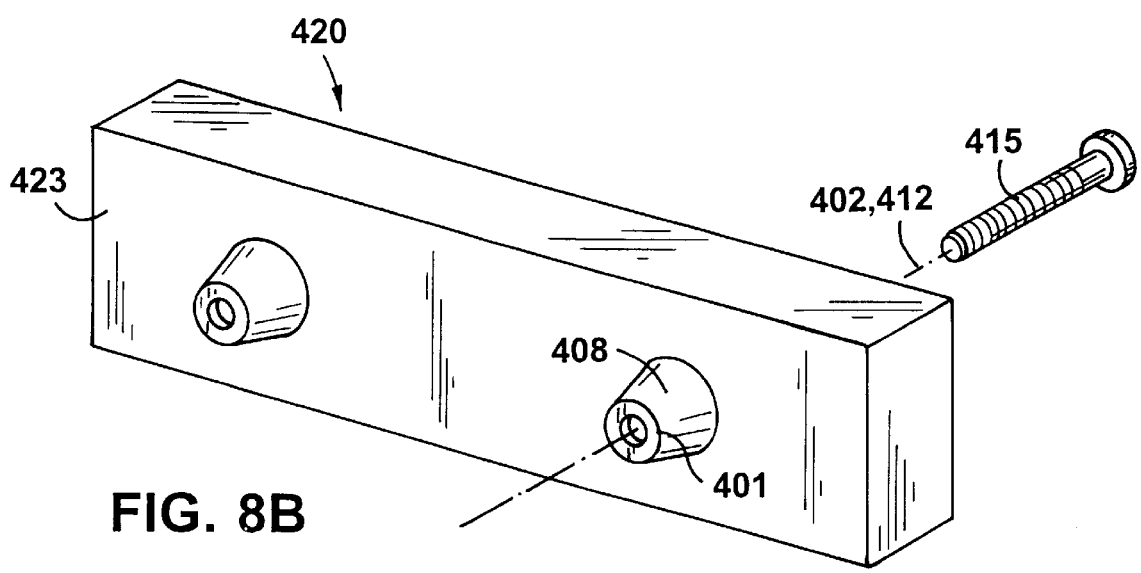
Figure 9:
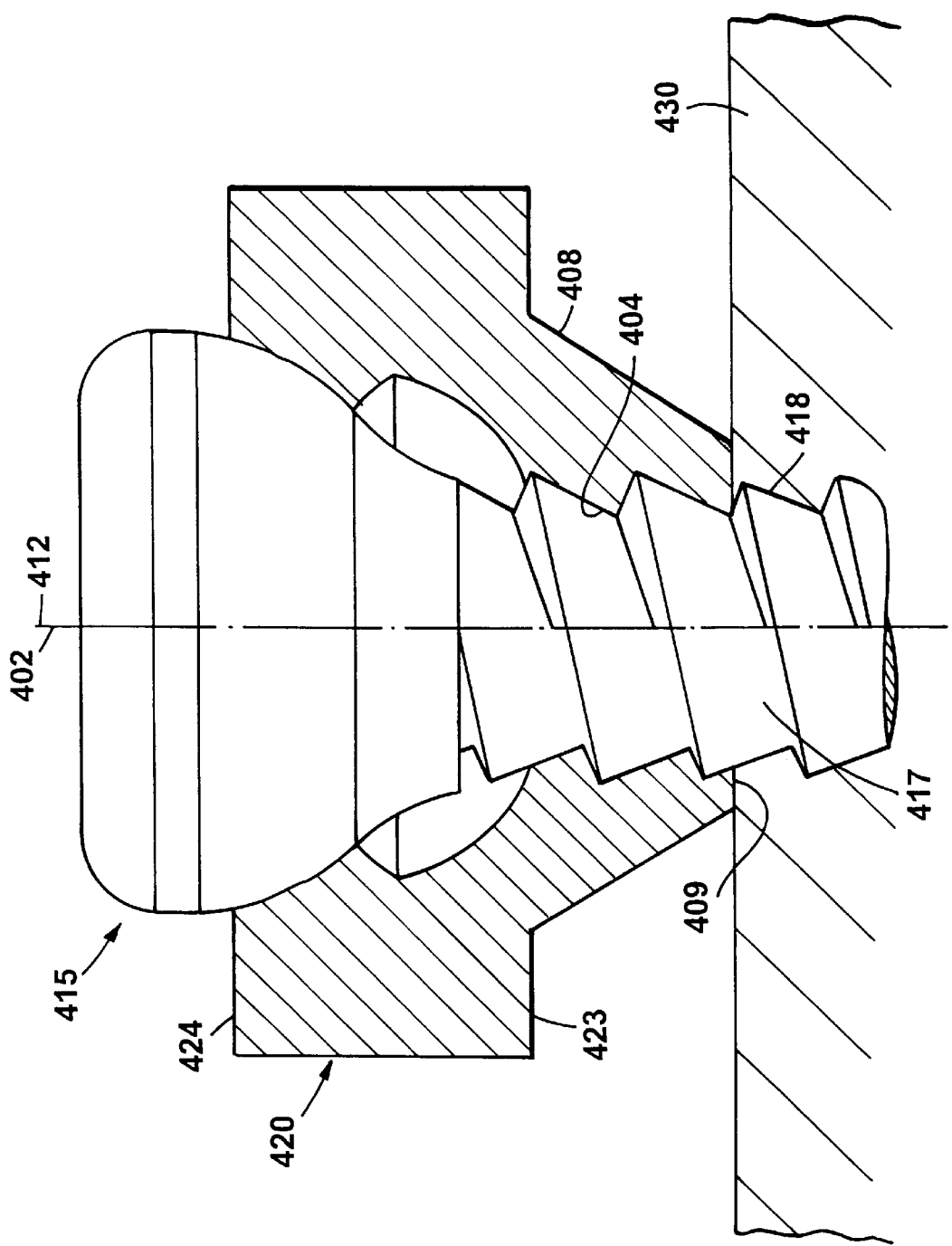
FIG. 9 shows a cross-section of an osteosynthetic system including the bone plate of FIG. 8.

According to another aspect of the invention, a bone plate and multiple lock washers can be made as a single integrally-formed unit. As illustrated in FIGS. 8–9, a bone plate 420 includes an upper surface 424 and a lower surface 423 and has multiple boreholes, such as the borehole 421, which extend through the plate 420 from the upper surface 424 to the lower surface 423. Each borehole 421 has a central axis 412. At least two of the boreholes, are provided with respective hollow protrusions, such as the protrusion 401, which projects beyond the lower surface 423 of the plate 420. The protrusion 401 has a ring or annular-shaped cross-section and a central axis 402 which is coaxial with the axis 412. The protrusion 401 is further provided with an interior or internal threading 404 for receiving a bone screw 415 inserted through the upper surface 424 of the plate 420. The outer surface 408 of the hollow protrusion 401 is tapered conically such that the outer diameter of the section of the protrusion 401 adjacent the lower surface 423 of the plate 420 is greater than the outer diameter at the free end of the protrusion 401. The free end of each protrusion can be adapted to abut the surface of a bone 430 to which the bone plate is to be fixed. In this manner, a relatively small contact surface 409 is provided for contact with the bone 430.

In general, the height of the protrusion 405 should be between approximately thirty to seventy percent the diameter of the borehole 421. Preferably, the height of the protrusion 401 is in the range from forty to sixty percent of the diameter of the borehole 421.

Other implementations are contemplated within the scope of the following claims.

What is claimed is:

1. An osteosynthetic bone plate having an upper surface, a lower surface, and boreholes extending through the bone plate from the upper surface to the lower surface, wherein each of at least two boreholes is provided with an integrally-formed hollow protrusion extending beyond said lower surface, and wherein each protrusion has an internal threading for receiving a bone screw inserted through the upper surface and borehole of the bone plate.

2. A bone plate according to claim 1 wherein the protrusions have an annular-shaped cross-section.

3. A bone plate according to claim 1 wherein the protrusions have an outer surface which is shaped conically.

4. A bone plate according to claim 1 wherein each protrusion has an outer diameter, and further has an end adjacent the lower surface of the bone plate and a free end, wherein the outer diameter is greater at the end adjacent the lower surface than at the free end.

5. A bone plate according to claim 4 wherein the outer diameter of each protrusion gradually tapers from the end of the protrusion adjacent the lower surface to the free end.

6. A bone plate according to claim 4 wherein the outer diameter of each protrusion increases from the free end to the end of the protrusion adjacent the lower surface.

7. A bone plate according to claim 1 wherein each borehole has a central axis and each corresponding hollow protrusion has a central axis, and wherein the central axes of each borehole and its protrusion are coaxial.

8. A bone plate according to claim 1 wherein each borehole has a diameter, and wherein the height of each protrusion is in the range between 30% and 70% of the diameter of the boreholes.

9. A bone plate according to claim 8 wherein the height of each protrusion is in the range between 40% and 60% of the diameter of the boreholes.

10. A bone plate according to claim 1 wherein each protrusion has an end adjacent the lower surface of the bone plate and a free end, wherein the free ends are adapted to abut a surface of a bone to which the bone plate is to be fixed.

11. A bone plate according to claim 1 wherein each protrusion has an end adjacent the lower surface of the bone plate and a free end, wherein the free ends are adapted to abut an outer surface of a bone to which the bone plate is to be fixed.

12. A bone plate according to claim 11 wherein the protrusions have an annular-shaped cross-section.

13. A bone plate according to claim 11 wherein the protrusions have an outer surface which is shaped conically.

14. A bone plate according to claim 11 wherein each protrusion has an outer diameter, and further has an end adjacent the lower surface of the bone plate and a free end, wherein the outer diameter is greater at the end adjacent the lower surface than at the free end.

15. A bone plate according to claim 14 wherein the outer diameter of each protrusion gradually tapers from the end of the protrusion adjacent the lower surface to the free end.

16. A bone plate according to claim 14 wherein the outer diameter of each protrusion increases from the free end to the end of the protrusion adjacent the lower surface.

17. A bone plate according to claim 11 wherein each borehole has a central axis and each corresponding hollow protrusion has a central axis, and wherein the central axes of each borehole and its protrusion are coaxial.

18. A bone plate according to claim 11 wherein each borehole has a diameter, and wherein the height of each protrusion is in the range between 30% and 70% of the diameter of the boreholes.

19. A bone plate according to claim 18 wherein the height of each protrusion is in the range between 40% and 60% of the diameter of the boreholes.

* * * * *